United States Patent
Hansen et al.

(10) Patent No.: US 11,682,924 B2
(45) Date of Patent: Jun. 20, 2023

(54) SYSTEMS AND METHODS FOR WIRELESS POWER RESONATORS WITH CORE CAVITY

(71) Applicant: TC1 LLC, St. Paul, MN (US)

(72) Inventors: John Freddy Hansen, Livermore, CA (US); Russell Anderson, Hopkins, MN (US); Daniel I. Harjes, Carlisle, MA (US); Alexander Baval, Milton, MA (US); Jeffrey Iudice, Lowell, MA (US)

(73) Assignee: TC1 LLC, St. Paul, MN (US)

( * ) Notice: Subject to any disclaimer, the term of this patent is extended or adjusted under 35 U.S.C. 154(b) by 0 days.

(21) Appl. No.: 17/341,818

(22) Filed: Jun. 8, 2021

(65) Prior Publication Data
US 2021/0384771 A1    Dec. 9, 2021

Related U.S. Application Data

(60) Provisional application No. 63/036,010, filed on Jun. 8, 2020.

(51) Int. Cl.
*H02J 50/12* (2016.01)
*H02J 50/00* (2016.01)

(52) U.S. Cl.
CPC .......... *H02J 50/12* (2016.02); *H02J 50/005* (2020.01); *H02J 2310/23* (2020.01)

(58) Field of Classification Search
CPC ...... H02J 50/12; H02J 50/005; H02J 2310/23; A61M 60/178; A61M 60/216; A61M 60/873; H01F 27/08; H01F 2027/2809; H01F 27/255; H01F 27/40; H01F 38/14; H01F 27/28; H01F 27/2804; H01F 27/2871
See application file for complete search history.

(56) References Cited

U.S. PATENT DOCUMENTS

| | | | |
|---|---|---|---|
| 9,737,264 B2 | 8/2017 | Braido et al. | |
| 10,373,756 B2 | 8/2019 | Hoarau et al. | |
| 2015/0290373 A1* | 10/2015 | Rudser | A61M 60/216 623/3.27 |
| 2015/0332841 A1* | 11/2015 | Hasegawa | H01F 5/00 307/104 |
| 2016/0347188 A1 | 12/2016 | Nakahara et al. | |
| 2017/0259677 A1* | 9/2017 | Stewing | H01F 38/14 |

(Continued)

FOREIGN PATENT DOCUMENTS

WO    2018190729 A1    10/2018

OTHER PUBLICATIONS

International Search Report and Written Opinion for International Patent Application No. PCT/US2021/036306, dated Sep. 30, 2021, 14 pages.

*Primary Examiner* — Lincoln D Donovan
*Assistant Examiner* — Alex W Lam
(74) *Attorney, Agent, or Firm* — Armstrong Teasdale LLP

(57) ABSTRACT

A resonator for use in a wireless power transfer system is provided. The resonator includes a core including a front surface, a back surface, and an annular sidewall extending between the front surface and the back surface, wherein an annular groove is defined in the front surface and surrounds a post, and wherein a cavity is defined in the back surface, the post and the cavity aligned with a longitudinal axis of the core. The resonator further includes a coil element disposed within the annular groove.

20 Claims, 6 Drawing Sheets

(56) References Cited

U.S. PATENT DOCUMENTS

| | | |
|---|---|---|
| 2019/0019613 A1* | 1/2019 | Navarro Pérez ........ H01F 27/32 |
| 2019/0076587 A1 | 3/2019 | Rudser et al. |
| 2019/0290923 A1 | 9/2019 | Yeh et al. |
| 2019/0321103 A1 | 10/2019 | Ben-Oren et al. |
| 2020/0139138 A1 | 5/2020 | Sit et al. |
| 2021/0000515 A1 | 1/2021 | Bonutti et al. |
| 2021/0036736 A1 | 2/2021 | Uchimura et al. |

\* cited by examiner

SYSTEMS AND METHODS FOR WIRELESS POWER RESONATORS WITH CORE CAVITY

CROSS-REFERENCE TO RELATED APPLICATIONS

This application claims priority to provisional application Ser. No. 63/036,010, filed Jun. 8, 2020, which is incorporated herein by reference in its entirety.

BACKGROUND OF THE DISCLOSURE a. Field of the Disclosure

The present disclosure relates generally to wireless power transfer systems, and more specifically, relates to wireless power transfer resonators including a cavity formed in a core of the resonator.

b. Background

Ventricular assist devices, known as VADs, are implantable blood pumps used for both short-term (i.e., days or months) and long-term (i.e., years or a lifetime) applications where a patient's heart is incapable of providing adequate circulation, commonly referred to as heart failure or congestive heart failure. A patient suffering from heart failure may use a VAD while awaiting a heart transplant or as a long term destination therapy. In another example, a patient may use a VAD while recovering from heart surgery. Thus, a VAD can supplement a weak heart (i.e., partial support) or can effectively replace the natural heart's function.

A wireless power transfer system may be used to supply power to the VAD. The wireless power transfer system generally includes an external transmit resonator and an implantable receive resonator configured to be implanted inside a patient's body. This power transfer system may be referred to as a transcutaneous energy transfer system (TETS).

To improve operation of wireless power transfer systems, it is generally desirable to reduce the amount of heat generated by the resonators and to reduce the size of the resonators. In particular, it would be advantageous to reduce the amount of heat generated during operation by the implantable receive resonator, and to reduce the size of the implantable receive resonator.

SUMMARY OF THE DISCLOSURE

The present disclosure is directed to a resonator for use in a wireless power transfer system. The resonator includes a core including a front surface, a back surface, and an annular sidewall extending between the front surface and the back surface, wherein an annular groove is defined in the front surface and surrounds a post, and wherein a cavity is defined in the back surface, the post and the cavity aligned with a longitudinal axis of the core. The resonator further includes a coil element disposed within the annular groove.

The present disclosure is further directed to a wireless power transfer system. The wireless power transfer system includes a power source, a transmit resonator electrically coupled to the power source, a load, and an implantable receive resonator electrically coupled to the load, the implantable receive resonator configured to receive wireless power from the transmit resonator. The implantable receive resonator includes a core including a front surface, a back surface, and an annular sidewall extending between the front surface and the back surface, wherein an annular groove is defined in the front surface and surrounds a post, and wherein a cavity is defined in the back surface, the post and the cavity aligned with a longitudinal axis of the core. The implantable receive resonator further includes a coil element disposed within the annular groove.

The present disclosure is further directed to a method of assembling a wireless power transfer system. The method includes electrically coupling a power source to an external transmit resonator, and electrically coupling a load to an implantable receive resonator, the implantable receive resonator configured to receive wireless power from the transmit resonator, the implantable receive resonator including a core including a front surface, a back surface, and an annular sidewall extending between the front surface and the back surface, wherein an annular groove is defined in the front surface and surrounds a post, and wherein a cavity is defined in the back surface, the post and the cavity aligned with a longitudinal axis of the core.

DETAILED DESCRIPTION OF THE DISCLOSURE

The present disclosure is directed to systems and methods for wireless power transfer resonators. A resonator includes a core including a front surface, a back surface, and an annular sidewall extending between the front surface and the back surface, wherein an annular groove is defined in the front surface and surrounds a post, and wherein a cavity is defined in the back surface, the post and the cavity aligned with a longitudinal axis of the core. The resonator further includes a coil element disposed within the annular groove.

Figure 1:
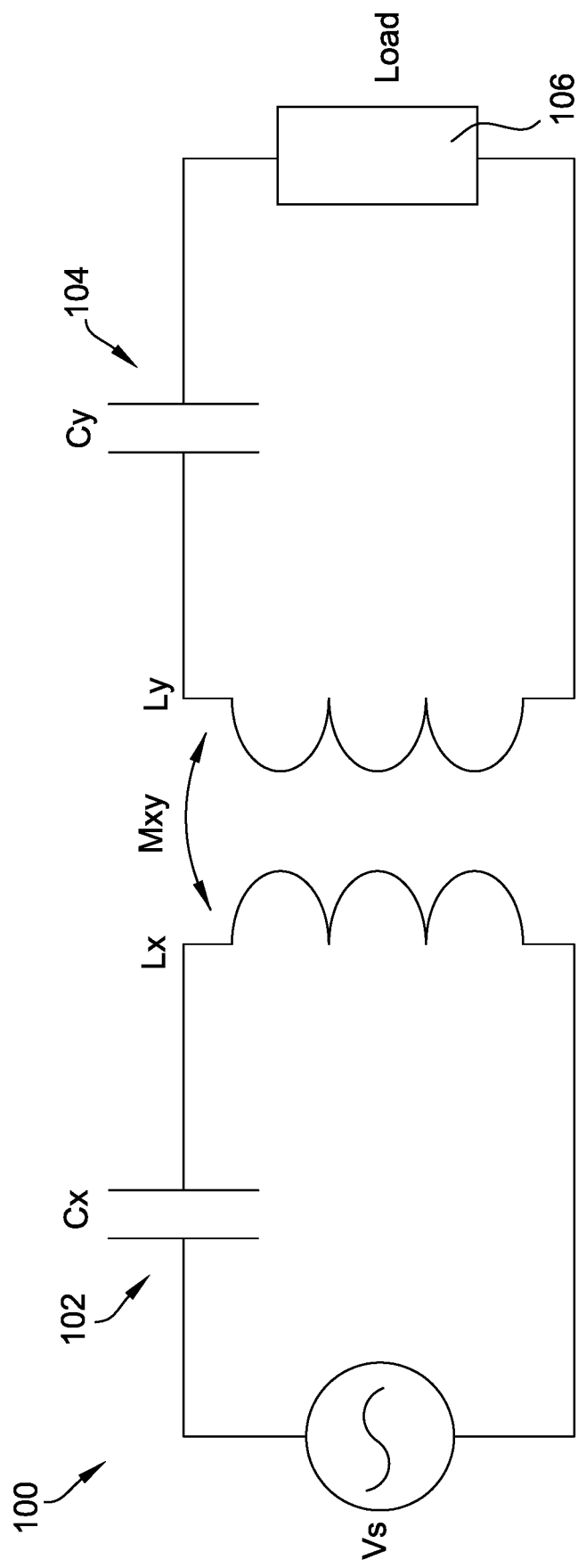
FIG. 1 is a simplified electrical circuit diagram of one embodiment of a wireless power transfer system.

Referring now to the drawings, FIG. 1 is a simplified circuit of an exemplary wireless power transfer system 100. The system 100 includes an external transmit resonator 102 and an implantable receive resonator 104. In the system shown in FIG. 1, a power source Vs is electrically connected with the transmit resonator 102, providing power to the transmit resonator 102. The receive resonator 104 is connected to a load 106 (e.g., an implantable medical device). The receive resonator 104 and the load 106 may be electrically connected with a switching or rectifying device (not shown).

In the exemplary embodiment, the transmit resonator 102 includes a coil Lx connected to the power source Vs by a capacitor Cx. Further, the receive resonator 104 includes a coil Ly connected to the load 106 by a capacitor Cy. Inductors Lx and Ly are coupled by a coupling coefficient k.

$M_{xy}$ is the mutual inductance between the two coils. The mutual inductance, $M_{xy}$, is related to the coupling coefficient k as shown in the below Equation (1).

$$M_{xy}=k\sqrt{L_x \cdot L_y} \quad (1)$$

In operation, the transmit resonator 102 transmits wireless power received from the power source Vs. The receive resonator 104 receives the power wirelessly transmitted by the transmit resonator 102, and transmits the received power to the load 106.

Figure 2:
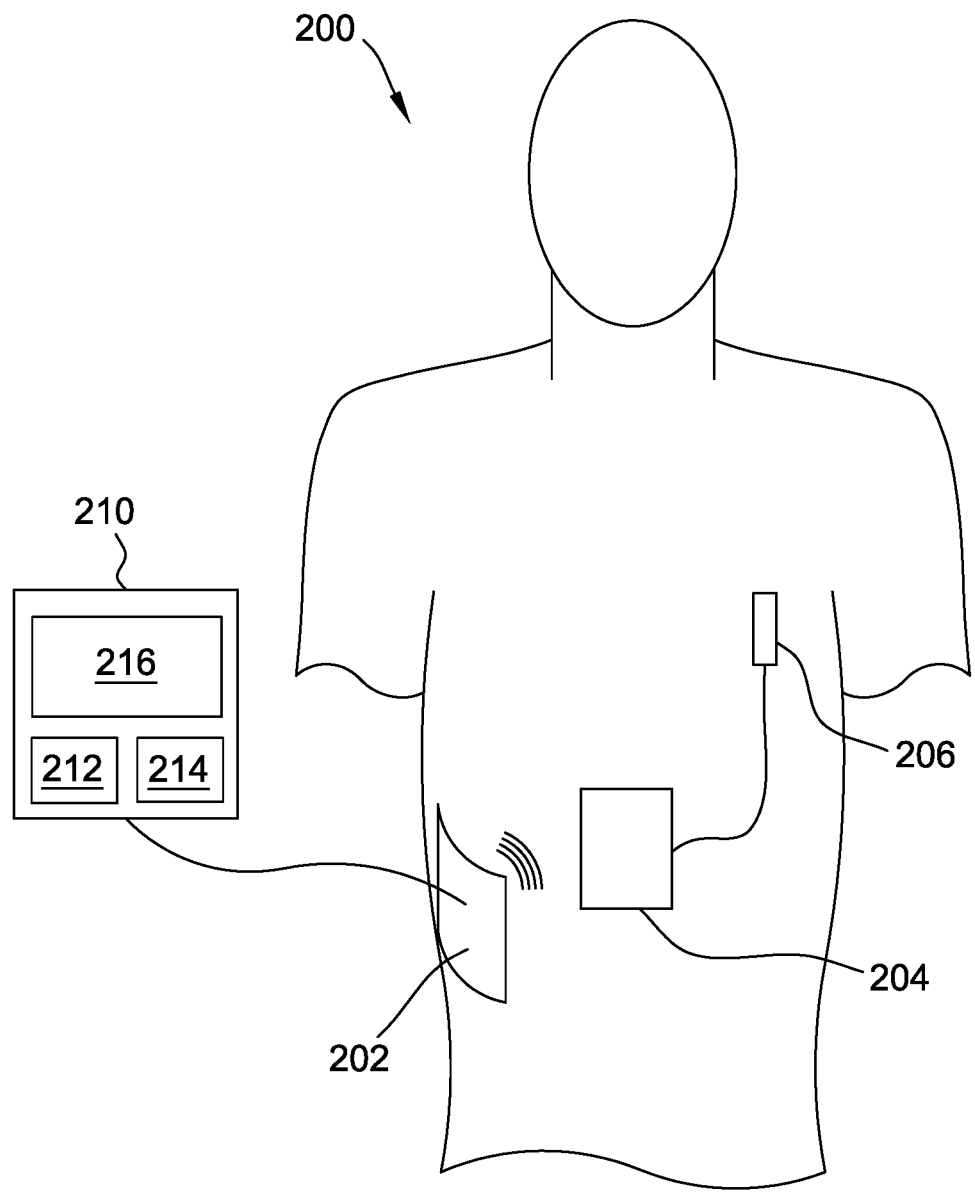
FIG. 2 is an illustration of the wireless power transfer system of FIG. 1 being used to supply power to a ventricular assist device (VAD).

FIG. 2 illustrates one embodiment of a patient 200 using an external coil 202 (such as the transmit resonator 102 shown in FIG. 1) to wirelessly transmit power to an implanted coil 204 (such as the receive resonator shown in FIG. 1). The implanted coil 204 uses the received power to power an implanted device 206. For example, the implanted device 206 may include a pacemaker or heart pump (e.g., a left ventricular assist device (LVAD)). In some embodiments, the implanted coil 204 and/or the implanted device 206 may include or be coupled to a battery.

In one embodiment, the external coil 202 is communicatively coupled to a computing device 210, for example, via wired or wireless connection, such that the external coil 202 may receive signals from and transmit signals to the computing device 210. In some embodiments, the computing device 210 is a power source for the external coil 202. In other embodiments, the external coil 202 is coupled to an alternative power supply (not shown). The computing device 210 includes a processor 212 in communication with a memory 214. In some embodiments, executable instructions are stored in the memory 214.

The computing device 210 further includes a user interface (UI) 216. The UI 216 presents information to a user (e.g., the patient 200). For example, the UI 216 may include a display adapter (not shown) that may be coupled to a display device, such as a cathode ray tube (CRT), a liquid crystal display (LCD), an organic LED (OLED) display, and/or an "electronic ink" display. In some embodiments, the UI 216 includes one or more display devices. Further, in some embodiments, presentation interface may not generate visual content, but may be limited to generating audible and/or computer-generated spoken-word content. In the example embodiment, the UI 216 displays one or more representations designed to aid the patient 200 in placing the external coil 202 such that the coupling between the external coil 202 and the implanted coil 204 is optimal. In some embodiments, the computing device 210 may be a wearable device. For example, in one embodiment, the computing device 210 is a wrist watch, and the UI 216 is displayed on the wrist watch.

Figure 3:
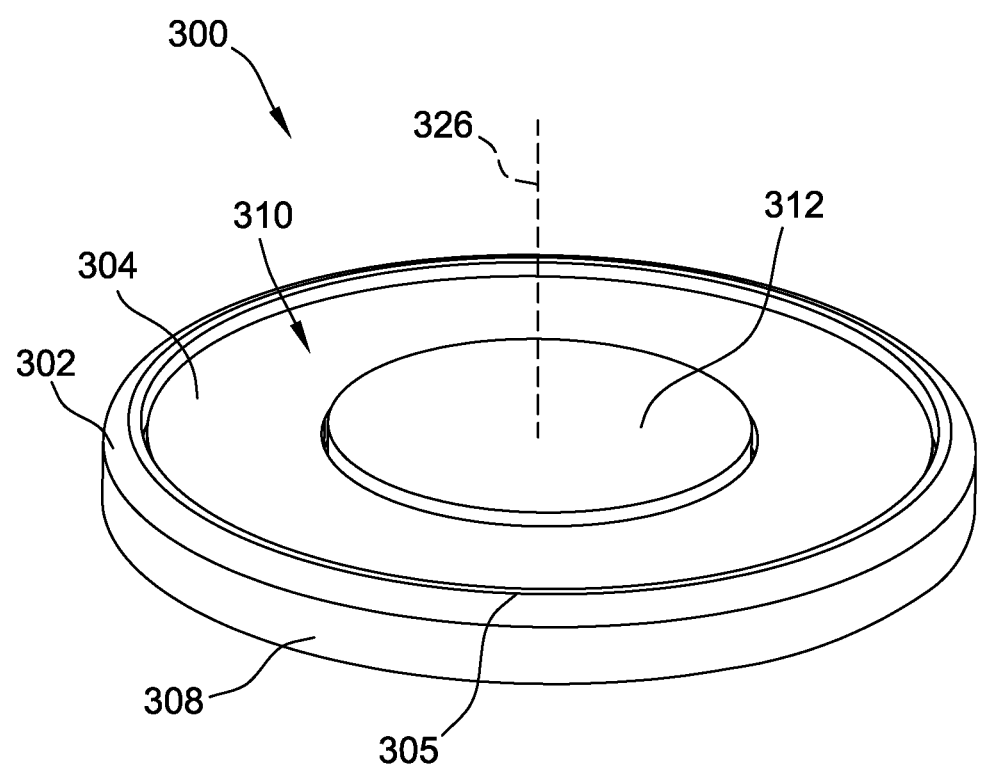
FIG. 3 is a front perspective view of one embodiment of a resonator that may be used to implement the system shown in FIG. 1.
Figure 4:
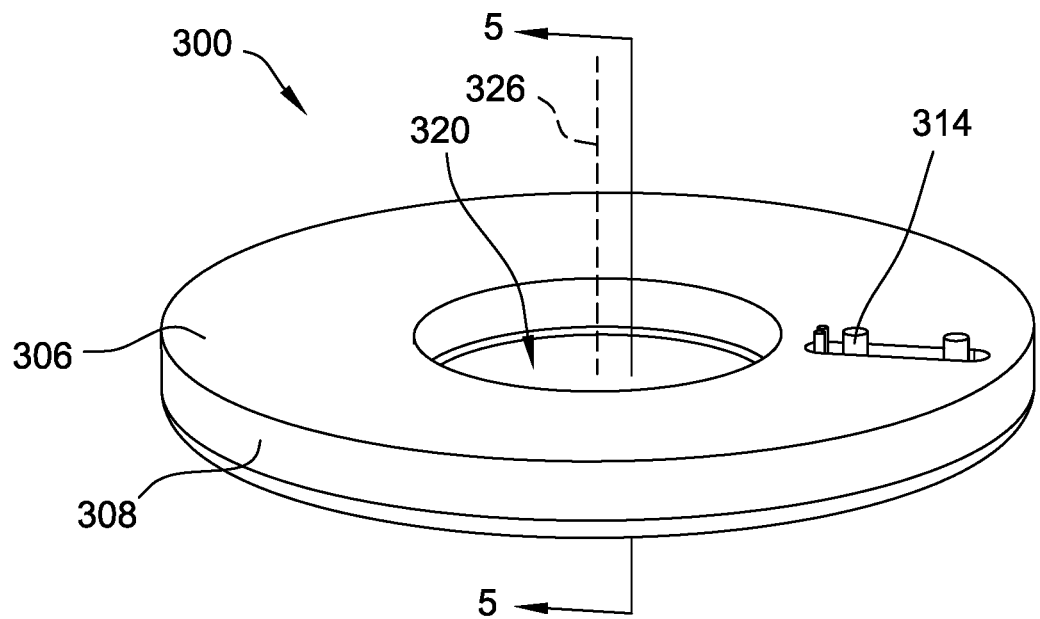
FIG. 4 is a back perspective view of the resonator shown in FIG. 3.

FIG. 3 is a front perspective view of one embodiment of a resonator 300 that may be used to implement the system 100 shown in FIG. 1. For example, the resonator 300 may be used to implement the external transmit resonator 102, the implantable receive resonator 104, the external coil 202, and/or the implanted coil 204. FIG. 4 is a back perspective view of the resonator 300, and FIG. 5 is a cross-sectional view of the resonator 300 taken along line 5-5 (shown in FIG. 4).

Figure 5:
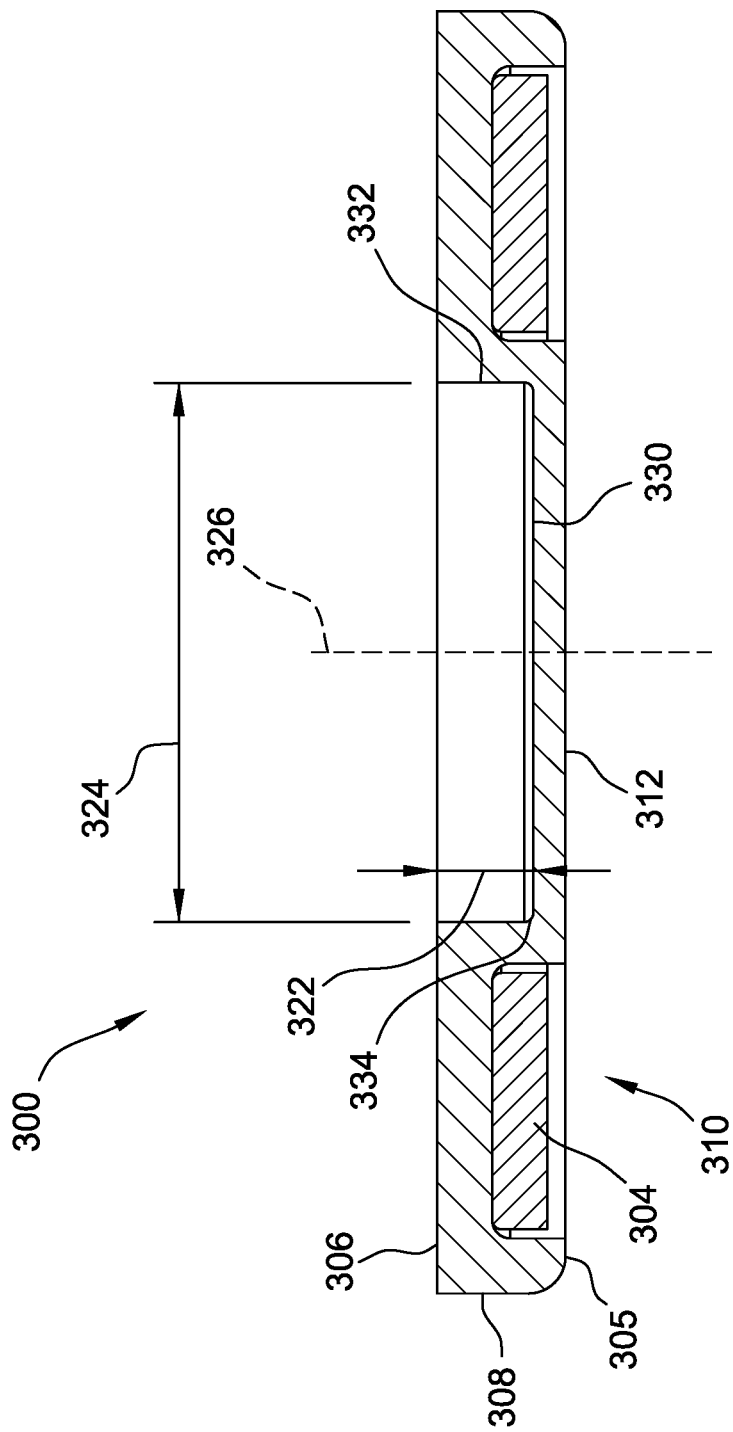
FIG. 5 is a cross-sectional view of the resonator shown in FIGS. 3 and 4 taken along line 5-5 (shown in FIG. 4).

As shown in FIGS. 3-5, the resonator 300 includes a core 302 and a coil element 304. The core 302 includes a front surface 305, a back surface 306, and an annular sidewall 308 extending between the front surface 305 and the back surface 306. An annular groove 310 is defined in the front surface 305, forming a central post 312 of the core 302.

The resonator 300 (including the core 302 and the coil element 304) functions as a wireless power resonator when coupled to a capacitor (e.g., a capacitor on a printed circuit board electrically coupled to the coil element 304). However, those of skill in the art will appreciate that the resonator 300, without connection to a capacitor, constitutes a coil assembly. Accordingly, as used herein, the term "resonator" does not require that the device be coupled to a capacitor to form a wireless power resonator. In contrast, as used herein, the term "resonator" is broad enough to cover a coil assembly that includes a core and a coil element without connection to a capacitor, as shown in FIG. 3.

The core 302 is formed of a magnetic material, and may, for example, be formed of a ferrite material, such as nickel-based or manganese-based ferrites. Nickel-based ferrites generally have lower electrical conductivity and reduced losses, while manganese-based ferrites have a higher magnetic permeability (while still having acceptable losses), facilitating containing magnetic field lines, and reducing fringing fields entering nearby conductors (e.g., a titanium enclosure or copper in a nearby PCB) to prevent losses. In other embodiments, other types of ferrite materials may be used. For example, in some embodiments, a magnesium-based ferrite (e.g., MgCuZn, which may outperform nickel-based and manganese-based ferrites in a frequency range around 1 Megahertz (MHz)) may be used.

In the embodiment shown, the coil element 304 is positioned within the annular groove 310 and surrounds the central post 312. The resonator 300 may be, for example, a Litz wire resonator or a stacked plate resonator. In a Litz wire resonator, the coil element 304 includes a plurality of loops of Litz wire. In a stacked plate resonator, the coil element 304 includes a plurality of stacked plates that may include a plurality of alternating dielectric layers and conductive layers arranged in a stack. The dielectric layers may be formed of, for example, ceramic, plastic, glass, and/or mica.

The coil element 304 is electrically coupled to, for example, a power source (when functioning as a transmit resonator) or the load 106 (when functioning as a receive resonator). In operation, when power is supplied to the resonator 300 operating as a transmit resonator, current flows through the coil element 304, creating an inductive current loop. This inductive current loop is capable of wirelessly transmitting power to a second resonator 300, provided that resonance frequencies of the first and second resonators 300 overlap. In the embodiment shown, the coil element 304 includes a plurality of terminals 314 that extend through the core to the rear surface 306. The terminals 314 facilitate electrically coupling the coil element 304 to a power supply or load, as appropriate.

As shown in FIGS. 3-5, a cavity 320 is defined in the rear surface 306. In the embodiment shown, the cavity 320 is a generally cylindrical cavity having a depth 322 and a diameter 324. The depth 322 of the cavity 320 may be, for example, approximately 4 millimeters (mm), and the diameter 324 of the cavity 320 may be, for example approximately 20 mm. Alternatively, the cavity 320 may have any suitable dimensions. Further, the cavity 320 (along with the post 312) is aligned with a longitudinal axis 326 of the resonator 300.

The cavity 320 is defined by a cavity sidewall 330 and a bottom wall 332. In the embodiment shown, the cavity sidewall 330 is generally annular and is oriented perpendicular to the bottom wall 332, and the cavity sidewall 330 and the bottom wall 332 meet at a rounded or chamfered interface 334. In other embodiments, the cavity sidewall 330 and the bottom wall 332 may have any suitable orientation.

For example, in some embodiment, the interface 334 forms a right angle between the cavity sidewall 330 and the bottom wall 332.

As described herein, the cavity 320 provides several advantages for the resonator 300, as compared to a resonator that does not include the cavity 320 (i.e., a resonator with a continuous, planar rear surface). Notably, the cavity 320 may be utilized whether the resonator 300 is a receive resonator or a transmit resonator.

For instance, the resonator 300 including the cavity 320 generates less heat during operation (e.g., during wireless power transfer) than a resonator that does not include the cavity 320. For example, in a computer modeling simulation, an implanted resonator (i.e., operating as a receiver) that did not include the cavity 320 increased the local tissue temperature by 5.68° C., while the resonator 300 increased the local tissue temperature by only 5.44° C. This reduction in heat is due, at least in part, to the removal of a portion of the material of the core 302.

From the computer modeling simulation, it was determined that the reduced temperature increase was due to an increase in heat at the back side (i.e., proximate the rear surface 306) of the resonator 300. Specifically, without the cavity 320, a front side of a receive resonator typically has a higher temperature than a back side, at least partly because the front side of the receive resonator faces the transmit resonator. Diverting heat to the back side (by implementing the cavity 320) increases the heat at the back side of the resonator 300 but reduces the heat at the front side of the resonator 300 for an overall reduction in heat at the resonator 300.

Generating less heat in an implanted device is generally desirable, as it reduces the impact the implanted device has on neighboring tissue. The resonator 300 including the cavity 320 also weighs less than a corresponding resonator without the cavity 320 (due to the absence of the material of the core 302 within the cavity 320). The cavity 320 may be filled with air or another suitable gas. For example, in some embodiments, the cavity 320 is filled with a gas that facilitates transferring heat from the front side to the back side of the resonator 300.

Notably, incorporating the cavity 320 into the resonator 300 does not significantly impact the electromagnetic properties of the resonator 300. That is, incorporating the cavity 320 does not impair the ability of the resonator 300 to transmit or receive wireless power. This is due to the magnetic field strength at the location of the cavity 320 being relative low. That is, due to the geometry of the resonator 300, during operation, only a relatively weak magnetic field is generated at the location of the cavity 300. For example, in one experimental simulation, the magnetic field strength in the cavity 320 was 5 micro tesla ($\mu$T), while the magnetic field strength outside the annular sidewall 308 was approximately fifty times greater. Further, by modifying the geometry of the resonator 300, the cavity 320 may also facilitate eliminating or reducing standing waves of closed-loop magnetic field lines that would otherwise be generated during operation of the resonator 300.

In at least some embodiments, one or more electronics components (not shown) are positioned within the cavity 320. Because the magnetic field strength is relatively low within the cavity 320, electronics components located within the cavity 320 are substantially shielded during operation of the resonator 300. That is, when electronics components are positioned within the cavity 320, operation of the resonator 300 does not electromagnetically impair or otherwise interfere with the operation of those electronics components.

Electronics components within the cavity 320 may be electronically coupled to the coil element 304 (e.g., via the terminals 314) and may include, for example, rectification circuitry (e.g., field effect transistors, diodes), matching capacitors, and/or series inductors. Alternatively, the electronics components may be any suitable electronics components.

If the electronics components in the cavity 320 generate heat (e.g., on the order of 300 milliwatts (mW)), the cavity 320 may be potted with a thermally insulating material, in order to channel the heat generated by the electronics components towards the rear of the resonator 300. Simulations have shown that such potting may reduce the maximum tissue temperature by at least 0.11° C. The more heat generated by the electronics components, the greater the benefits provided by such potting.

Including electronics components in the cavity 320 facilitates reducing the overall size of the resonator 300. That is, if the electronics components are not located in the cavity 320 (e.g., in embodiments that do not include the cavity 320), those components must be located external to the core 302, increasing the size of the resonator 300.

In some embodiments, the resonator 300 includes a cover (not shown) that encloses and protects electronics components within the cavity 320. The cover may be substantially coplanar with rear surface 306 and may be made of the same material as the core 302.

Those of skill in the art will appreciate that the dimensions and structure of the resonator 300 described herein are merely examples. For example, in some embodiments, the dimensions of the core 302 and the cavity 320 may be altered to minimize losses (e.g., at a given operating frequency of the resonator 300).

Figure 6:
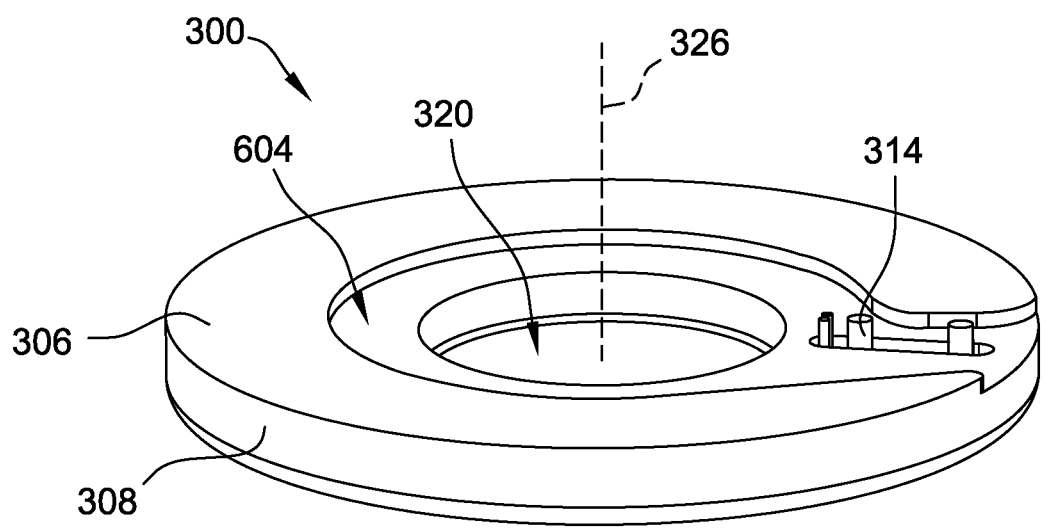
FIG. 6 is a back perspective view of an alternative resonator that may be used to implement the system shown in FIG. 1.

FIG. 6 is a back perspective view of an alternative resonator 600. Unless otherwise indicated, resonator 600 is substantially similar to resonator 300, and like reference numerals are used to designate like components. In this embodiment, in addition to the cavity 302, a recess 604 is defined in the rear surface 306 of the resonator 600. The recess 604 is generally wider than the cavity 320, but shallower than the cavity 320. Accordingly, relatively thin components may be positioned within the recess 604, such as a printed circuit board (PCB) connected to the terminals 314.

The embodiments described herein are directed to systems and methods for wireless power transfer resonators. A resonator includes a core including a front surface, a back surface, and an annular sidewall extending between the front surface and the back surface, wherein an annular groove is defined in the front surface and surrounds a post, and wherein a cavity is defined in the back surface, the post and the cavity aligned with a longitudinal axis of the core. The resonator further includes a coil element disposed within the annular groove.

Although the embodiments and examples disclosed herein have been described with reference to particular embodiments, it is to be understood that these embodiments and examples are merely illustrative of the principles and applications of the present disclosure. It is therefore to be understood that numerous modifications can be made to the illustrative embodiments and examples and that other arrangements can be devised without departing from the spirit and scope of the present disclosure as defined by the claims. Thus, it is intended that the present application cover the modifications and variations of these embodiments and their equivalents.

This written description uses examples to disclose the disclosure, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A resonator for use in a wireless power transfer system, the resonator comprising:
   a core comprising:
      a front surface;
      a back surface; and
      an annular sidewall extending between the front surface and the back surface, wherein an annular groove is defined in the front surface, surrounds a post, and extends from the front surface to a groove bottom wall, and wherein a cavity is defined in the back surface and extends from the back surface, beyond the groove bottom wall, to a cavity bottom wall, such that the cavity bottom wall is closer to the front surface than the groove bottom wall, the post and the cavity aligned with a longitudinal axis of the core; and
   a coil element disposed within the annular groove.

2. The resonator of claim 1, further comprising at least one electronics component disposed within the cavity.

3. The resonator of claim 2, wherein the cavity is potted with a thermally insulating material configured to channel heat generated by the at least one electronics component toward a rear of the resonator.

4. The resonator of claim 1, wherein the cavity has a diameter of approximately 20 millimeters and a depth of approximately 4 millimeters.

5. The resonator of claim 1, wherein the resonator comprises an implantable receive resonator.

6. The resonator of claim 1, wherein the resonator comprises an external transmit resonator.

7. The resonator of claim 1, wherein the coil element comprises a plurality of stacked plates.

8. The resonator of claim 1, wherein the coil element comprises a plurality of loops of Litz wire.

9. The resonator of claim 1, wherein a recess is defined in the back surface, and wherein the recess is shallower than the cavity.

10. The resonator of claim 1, wherein the cavity is filled with a gas that facilitates transferring heat from a front of the resonator to a back of the resonator.

11. A wireless power transfer system comprising:
   a power source;
   a transmit resonator electrically coupled to the power source;
   a load; and
   an implantable receive resonator electrically coupled to the load, the implantable receive resonator configured to receive wireless power from the transmit resonator, the implantable receive resonator comprising:
      a core comprising:
         a front surface;
         a back surface; and
         an annular sidewall extending between the front surface and the back surface, wherein an annular groove is defined in the surface, surrounds a post, and extends from the front surface to a groove bottom wall, and wherein a cavity is defined in the back surface and extends from the back surface, beyond the groove bottom wall, to a cavity bottom wall, such that the cavity bottom wall is closer to the front surface than the groove bottom wall, the post and the cavity aligned with a longitudinal axis of the core; and
      a coil element disposed within the annular groove.

12. The wireless power transfer system of claim 11, wherein the resonator further comprises at least one electronics component disposed within the cavity.

13. The wireless power transfer system of claim 11, wherein the cavity is defined by an annular cavity sidewall and a bottom wall.

14. The wireless power transfer system of claim 13, wherein the cavity has a diameter of approximately 20 millimeters and a depth of approximately 4 millimeters.

15. The wireless power transfer system of claim 11, wherein the coil element comprises a plurality of stacked plates.

16. The wireless power transfer system of claim 11, wherein the coil element comprises a plurality of loops of Litz wire.

17. The wireless power transfer system of claim 11, wherein a recess is defined in the back surface, and wherein the recess is shallower than the cavity.

18. The wireless power transfer system of claim 11, wherein the cavity is filled with a gas that facilitates transferring heat from a front of the resonator to the back of the resonator.

19. A method of assembling a wireless power transfer system, the method comprising:
   electrically coupling a power source to an external transmit resonator; and
   electrically coupling a load to an implantable receive resonator, the implantable receive resonator configured to receive wireless power from the transmit resonator, the implantable receive resonator including a core including a front surface, a back surface, and an annular sidewall extending between the front surface and the back surface, wherein an annular groove is defined in the front surface, surrounds a post, and extends from the front surface to a groove bottom wall, and wherein a cavity is defined in the back surface and extends from the back surface, beyond the groove bottom wall, to a cavity bottom wall, such that the cavity bottom wall is closer to the front surface than the groove bottom wall, the post and the cavity aligned with a longitudinal axis of the core.

20. The method of claim 19, further comprising positioning at least one electronics component within the cavity.

* * * * *